(12) United States Patent
Kuo et al.

(10) Patent No.: US 11,766,465 B2
(45) Date of Patent: Sep. 26, 2023

(54) EXTERNAL COMPOSITION FOR WOUND HEALING CONTAINING LACTOBACILLUS FERMENTATION PRODUCT AND METHOD FOR PROMOTING WOUND HEALING USING THE SAME

(71) Applicant: GRAPE KING BIO LTD, Taoyuan (TW)

(72) Inventors: Hsing-Chun Kuo, Taoyuan (TW); Chin-Chu Chen, Taoyuan (TW); Yen-Lien Chen, Taoyuan (TW); Shih-Wei Lin, Taoyuan (TW); Yen-Po Chen, Taoyuan (TW); Ci-Sian Wang, Taoyuan (TW); Yu-Hsin Hou, Taoyuan (TW); Yang-Tzu Shih, Taoyuan (TW); Ching-Wen Lin, Taoyuan (TW); Ya-Jyun Chen, Taoyuan (TW); Jia-Lin Jiang, Taoyuan (TW); You-Shan Tsai, Taoyuan (TW); Zi-He Wu, Taoyuan (TW)

(73) Assignee: GRAPE KING BIO LTD, Taoyuan (TW)

(*) Notice: Subject to any disclaimer, the term of this patent is extended or adjusted under 35 U.S.C. 154(b) by 0 days.

(21) Appl. No.: 17/514,670

(22) Filed: Oct. 29, 2021

(65) Prior Publication Data
US 2022/0152129 A1   May 19, 2022

(30) Foreign Application Priority Data

Nov. 13, 2020 (TW) .................. 109139743

(51) Int. Cl.
*A61K 35/747* (2015.01)
*A61P 17/02* (2006.01)
*A61K 9/00* (2006.01)

(52) U.S. Cl.
CPC .......... *A61K 35/747* (2013.01); *A61K 9/0014* (2013.01); *A61P 17/02* (2018.01)

(58) Field of Classification Search
None
See application file for complete search history.

(56) References Cited

U.S. PATENT DOCUMENTS

| 4,743,442 A * | 5/1988 | Raaf .................. A61K 8/20 424/59 |
| 11,197,901 B2 * | 12/2021 | Chen ................ A61K 35/747 |

FOREIGN PATENT DOCUMENTS

| CN | 106573023 A | 4/2017 |
| JP | 2019214548 A | 12/2019 |
| JP | 2020059694 A | 4/2020 |
| JP | 2020080861 A | 6/2020 |
| TW | I634207 B | 9/2018 |
| TW | I636134 B | 9/2018 |
| TW | 201917206 A | 5/2019 |
| WO | 2020106099 A1 | 5/2020 |

OTHER PUBLICATIONS

Jessica Brandi, "Exploring the wound healing, anti-inflammatory, anti-pathogenic and proteomic effects of lactic acid bacteria on keratinocytes", Journal, 2020, 1-14, vol. 10, Scientific Reports.
Alberto N. Ramos, "Compounds from Lactobacillus plantarum culture supernatants with potential pro-healing and anti-pathogenic properties in skin chronic wounds", Journal, 2015, 350-358, vol. 53, No. 3, Pharmaceutical Biology.
Jia Sin Ong et al., "Lactobacillus plantarum USM8613 Aids in Wound Healing and Suppresses *Staphylococcus aureus* Infection at Wound Sites", Springer, Probiotics and Antimicrobial Proteins, 2019, vol. 12, pp. 125-137, 13 pages.
Ramos et al., "Compounds from Lactobacillus plantarum culture supernatants with potential pro-healing and anti-pathogenic properties in skin chronic wounds", Pharmaceutical Biology, 2014, vol. 53, Issue 3, 10 pages.

* cited by examiner

*Primary Examiner* — Vera Afremova
(74) *Attorney, Agent, or Firm* — Hayes Soloway PC

(57) ABSTRACT

The present disclosure relates to as external composition for wound healing containing a *Lactobacillus* fermentation product, which comprises a *Lactobacillus* fermentation product as an effective component. The *Lactobacillus* fermentation product is a bacteria-free concentrated filtrate from fermentation of *Lactobacillus plantarum* and the effective component is loaded onto a pharmaceutically acceptable absorbent carrier or carrying agent. The external composition for wound healing has anti-inflammatory and healing promoting effects on a skin wound after applied directly onto the skin wound.

5 Claims, 2 Drawing Sheets
(1 of 2 Drawing Sheet(s) Filed in Color)

EXTERNAL COMPOSITION FOR WOUND HEALING CONTAINING LACTOBACILLUS FERMENTATION PRODUCT AND METHOD FOR PROMOTING WOUND HEALING USING THE SAME

RELATED APPLICATIONS

This application claims priority to Taiwan Application Serial Number 109139743, filed Nov. 13, 2020, which is herein incorporated by reference.

BACKGROUND

Field of Invention

The present disclosure relates to a *Lactobacillus* fermentation product, and in particular, to an external composition for wound healing containing *Lactobacillus* fermentation product that has anti-inflammatory and wound healing promoting effects.

Description of Related Art

The skin is an organ with the largest surface area in the human body and also serves as the first immune barrier of the body to protect human health. When the skin is damaged, a series of wound repair and healing processes begin. Generally, the skin wound healing process involves three major phases, inflammation, new tissue formation and remodeling (Schilling, 1976). Wounds can be divided into acute wounds and chronic wounds according to the healing time. Typically, wounds can heal within one month. If a wound does not heal over more than four to six weeks, it is called a chronic wound.

In general, one of the common ways to treat skin wounds is to use wound dressings, which can promote wound healing and prevent infections and others. Skin wound dressings can be divided into three main categories, namely traditional fiber dressings, synthetic dressings and biological dressings (Shu & Weng, 2011).

*Lactobacillus* has been studied to have a variety of health effects on the human body, such as reducing cholesterol, enhancing immunity, and preventing or treating infections (Salminen et al., 2010; Settanni and Moschetti, 2010). Metabolites produced by *Lactobacillus* can be, for example, exopolysaccharide (EPS), which has also been studied to have various effects, such as improving immunity and anti-tumor activity (Arul et al., 2007; Shivanada et al., 2010). Rodrigues et al. (2004) have evaluated *Lactobacillus* and a polysaccharide thereof for use in wound healing in rats. The results have shown that a symbiotic mixture of *Lactobacillus* (e.g. kefir) and a polysaccharide thereof (e.g. kefiran extract) are given to show an antibacterial effect and a wound healing promoting effect. Zahedi et al. (2011) have applied an ointment made from the bacteria of plant *Lactobacillus* (accession number: GQ423760) containing high-yield EPS to skin wounds in rats and found that it can reduce inflammation and accelerate wound healing.

However, the above applications all contain the bacteria itself or bacterial components (such as polysaccharides). As for the use of metabolites from *Lactobacillus* fermentation in external preparations for skin wound healing, there are still relatively few studies. Therefore, it is very necessary to develop other effects and applications of metabolites from *Lactobacillus* fermentation.

SUMMARY

Thus, one aspect of the present disclosure is to provide an external composition for wound healing containing a *Lactobacillus* fermentation product, which comprises a *Lactobacillus* fermentation product and a pharmaceutically acceptable absorbent carrier or carrying agent, where the *Lactobacillus* fermentation product serves as an effective component, which is loaded onto the absorbent carrier or carrying agent.

Another aspect of the present disclosure is to provide a method of a *Lactobacillus* fermentation product in the preparation of an external composition for wound healing, which can effectively inhibit skin wound inflammation and promote wound healing.

According to the aspect of the present disclosure, an external composition for wound healing containing a *Lactobacillus* fermentation product is provided. In one embodiment, the external composition for wound healing can comprise a *Lactobacillus* fermentation product and a pharmaceutically acceptable absorbent carrier or carrying agent. In the embodiment, the *Lactobacillus* fermentation product serves as an effective component and can be a bacteria-free (i.e., no bacteria) concentrated filtrate from a fermentation step, a solid-liquid separation step and a concentration step of a fermentation substrate by *Lactobacillus*, and the *Lactobacillus* can be, for example, *Lactobacillus plantarum* GKM3 (deposited in Bioresource Collection and Research Center, Food Industry Research and Development Institute of the Republic of China, No. 331 Food Road, Hsinchu, Taiwan with deposit date of Jul. 14, 2017 and deposit number of BCRC 910787; and additionally deposited in China General Microbiological Culture Collection Center (CGMCC), No. 1, West Beichen Road, Chaoyang District, Beijing, China with deposit date of Aug. 25, 2017 and deposit number of CGMCC 14565 and confirmed to be alive on Aug. 25, 2017). In the embodiment, the absorbent carrier or carrying agent can be used to load the effective component.

According to one embodiment of the present disclosure, the fermentation substrate is selected from MRS agar, PCA agar, M17 agar, Rogosa agar, TOS-MUP agar, and any combination thereof. In this embodiment, the concentrated filtrate can be, for example, concentrated to 5% to 20% of an initial volume of the fermentation substrate. The absorbent carrier can include, but is not limited to, a fiber carrier, a breathable film carrier, a hydrogel carrier, a gel carrier, a foam carrier, an algin carrier, a protein carrier, and any combination thereof. In other examples, the carrying agent can include an atomizing agent, and the external composition for wound healing can be, for example, an aerosol.

According to one embodiment of the present disclosure, the *Lactobacillus* fermentation product has the effects of inhibiting skin wound inflammation and promoting wound healing.

According to one embodiment of the present disclosure, the effective component further comprises a medicinal component.

According to another aspect of the present disclosure, an external composition for wound healing containing a *Lactobacillus* fermentation product is provided. In one embodiment, the external composition for wound healing can comprise a *Lactobacillus* fermentation product and a pharmaceutically acceptable absorbent carrier or carrying agent. In the embodiment, the *Lactobacillus* fermentation product serves as an effective component and can be a bacteria-free concentrated filtrate from a fermentation step, a solid-liquid separation step and a concentration step of a fermentation substrate by *Lactobacillus*, the concentrated filtrate is concentrated to 5% to 20% of an initial volume of the fermentation substrate, and the *Lactobacillus* can be, for example, *Lactobacillus plantarum* GKM3 (deposited in Bioresource Collection and Research Center, Food Industry Research and Development Institute of the Republic of China, No. 331 Food Road, Hsinchu, Taiwan with deposit date of Jul. 14, 2017 and deposit number of BCRC 910787; and additionally deposited in China General Microbiological Culture Collection Center (CGMCC), No. 1, West Beichen Road, Chaoyang District, Beijing with deposit date of Aug. 25, 2017 and deposit number of CGMCC 14565 and confirmed to be alive on Aug. 25, 2017).

According to another aspect of the present disclosure, a method for promoting wound healing using an external composition is provided, where the *Lactobacillus* fermentation product serves as an effective component and can be a bacteria-free concentrated filtrate from a fermentation step, a solid-liquid separation step and a concentration step of a fermentation substrate by *Lactobacillus*, and the concentrated filtrate is concentrated to 5% to 20% of an initial volume of the fermentation substrate. The *Lactobacillus* is *L. plantarum* GKM3 (with deposit number of BCRC 910787). The external composition for wound healing can comprise a *Lactobacillus* fermentation product and a pharmaceutically acceptable absorbent carrier or carrying agent.

When the external composition for wound healing containing a *Lactobacillus* fermentation product of the present disclosure is applied, a bacteria-free concentrated filtrate from fermentation by a certain strain of *L. plantarum* is used as an effective component, so that the resulting external composition for wound healing has the effects of inhibiting skin wound inflammation and promoting wound healing after administered to a skin wound.

It is to be understood that both the foregoing general description and the following detailed description are by examples, and are intended to provide further explanation of the invention as claimed.

BRIEF DESCRIPTION OF THE DRAWINGS

The patent or application file contains at least one drawing executed in color. Copies of this patent or patent application publication with color drawings will be provided by Office upon request and payment of the necessary fee. The disclosure can be more fully understood by reading the following detailed description of the embodiment, with reference made to the accompanying drawings as follows.

DETAILED DESCRIPTION

Figure 1:
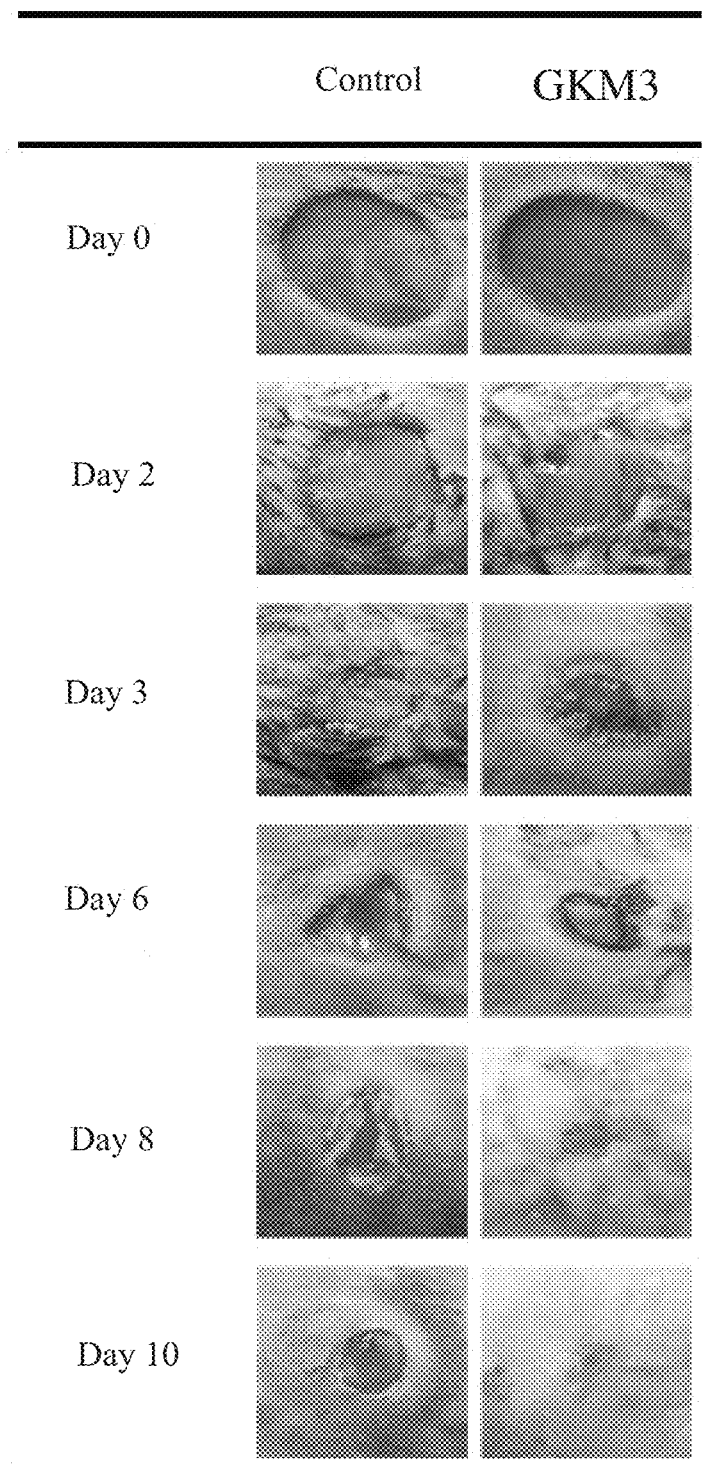
FIG. 1 shows the appearance changes of mouse skin wounds administered with a concentrated filtrate from probiotic GKM3 fermentation (GKM3 group) or saline (control group) at different time points according to one embodiment of the present disclosure.

Accordingly, the present disclosure provides an external composition for wound healing containing a *Lactobacillus* fermentation product, which comprises a *Lactobacillus* fermentation product as an effective component. The *Lactobacillus* fermentation product can be a bacteria-free (i.e., no bacteria) concentrated filtrate from fermentation of *Lactobacillus plantarum* and the effective component is loaded onto a pharmaceutically acceptable absorbent carrier or carrying agent.

Generally, the "*Lactobacillus* fermentation product" mentioned herein refers to a bacteria-free concentrated filtrate from a fermentation step, a solid-liquid separation step and a concentration step of a fermentation substrate by *Lactobacillus*. In other words, the present *Lactobacillus* fermentation product is substantially free of bacteria and bacteria components. Further, the fermentation step, solid-liquid separation step and concentration step above can use conventional process conditions rather than repetition herein.

The "*Lactobacillus*" mentioned herein refers to *Lactobacillus plantarum* GKM3 (deposited in Bioresource Collection and Research Center, Food Industry Research and Development Institute of the Republic of China, No. 331 Food Road, Hsinchu, Taiwan with deposit date of Jul. 14, 2017 and deposit number of BCRC 910787 and confirmed to be alive on Jul. 26, 2017). The strain GKM3 was additionally deposited in China General Microbiological Culture Collection Center (CGMCC), No. 1, West Beichen Road, Chaoyang District, Beijing, China, with deposit date of Aug. 25, 2017 and deposit number of CGMCC 14565 and confirmed to be alive on Aug. 25, 2017). Regarding the microbiological properties of the strain GKM3, refer to Taiwan Patent Publication No. 1634207, which is incorporated herein by reference. Due to the wide variety of *Lactobacillus* strains, there are significant differences between the properties of different strains. If *Lactobacillus plantarum* other than GKM3 is used for a fermentation step, a solid-liquid separation step and a concentration step on the fermentation substrate, in the absence of experimental confirmation, the resultant bacteria-free concentrated filtrate cannot be expected to have anti-inflammatory and healing promoting effects on skin wounds.

The "fermentation substrate" mentioned herein refers to those suitable for the culture of the strain GKM3, and is not particularly limited. In some examples, the fermentation substrate can be a commercially available medium, including but not limited to MRS agar, PCA agar, M17 agar, Rogosa agar, TOS-MUP agar, and any combination thereof. The MRS agar can also be optionally added with 3% NaCl or 0.05% bromocresol green. The bacteria density of the strain GKM3 inoculated into the fermentation substrate is not particularly limited. In some embodiments, the inoculation dose of the strain GKM3 can be, for example, $1 \times 10^{10}$ colony forming units (cfu)/mL to $1 \times 10^{11}$ cfu/mL, but the present disclosure is not limited thereto. In addition, the fermentation time of the strain GKM3 for the fermentation step of the fermentation substrate is not particularly limited. Generally, it can be, for example, 12 hours to 24 hours, but preferably is 16 hours to 20 hours.

The "concentrated filtrate" (also called fermented concentrated filtrate) mentioned herein refers to a filtrate after a fermentation step, a solid-liquid separation step, and a concentration step of a fermentation substrate by *Lactobacillus*, which is further concentrated to less than an initial volume of the fermentation substrate, so the concentration factor is not particularly limited. In some examples, the concentrated filtrate can be concentrated by 2 times to 20 times, which is equivalent to 5% to 50% of an initial volume of the fermentation substrate, but preferably is concentrated to 5% to 20% of the initial volume of the fermentation substrate.

The "absorbent carrier" or "carrying agent" mentioned herein is used to load the effective component, and the material thereof is not particularly limited, as long as it does not interfere with the effects of the effective component. Furthermore, the content of the *Lactobacillus* fermentation product loaded on the absorptive carrier or carrying agent is not particularly limited, depending on the product requirements and the loading capacity of the selected carrier or carrying agent.

In some example, a suitable absorbent carrier can include, but is not limited to, a fiber carrier, a breathable film carrier, a hydrogel carrier, a gel carrier, a foam carrier, an algin carrier, a protein carrier, and any combination thereof.

In other examples, a suitable carrier can be, for example, an atomizing agent, whereby an aerosol formulation of an external composition for wound healing is provided.

Compared with the conventional application of a composition containing bacteria itself or bacteria components (such as polysaccharides) to a wound, the present disclosure uses a bacteria-free concentrated filtrate, which can effectively reduce the unwanted irritation caused by the bacteria-related components on the wound. In one embodiment, it is confirmed via animal experiments that the *Lactobacillus* fermentation product indeed has anti-inflammatory and healing promoting effects on an animal skin wound after directly contacted with the wound, so it can be used as an effective component of an external composition for wound healing. In other embodiments, the effective component can optionally further comprise a medicinal component, and this medicinal component can be a conventional compound and/or agent rather than repetition herein. Furthermore, the present disclosure uses the conventional fermentation step, solid-liquid separation step and concentration step to prepare the *Lactobacillus* fermentation product, without changing the existing process and equipment, resulting in easy process, low cost and easy mass production.

In addition, the present disclosure also provides a method for promoting wound healing using an external composition is provided, where the *Lactobacillus* fermentation product serves as an effective component and can be a bacteria-free concentrated filtrate from a fermentation step, a solid-liquid separation step and a concentration step of a fermentation substrate by *Lactobacillus*, and the concentrated filtrate is concentrated to 5% to 20% of an initial volume of the fermentation substrate. The *Lactobacillus* is *L. plantarum* GKM3 (with deposit number of BCRC 910787). The external composition for wound healing can comprise a *Lactobacillus* fermentation product and a pharmaceutically acceptable absorbent carrier or carrying agent.

Thereinafter, several embodiments are used below to illustrate the application of the present disclosure, but they are not intended to limit the present disclosure. One of ordinary skill in the art of the present disclosure can make various changes and modifications without departing from the spirit and scope of the present disclosure.

Example 1: Establishing an Animal Model

1. Experimental Animals

First, 12 C57BL/6J male mice aged 8 to 10 weeks from the National Laboratory Animal Center (NLAC) were housed in the Animal Center of Chang Gung Memorial Hospital, Chiayi. An animal room was kept at a temperature of 22±2° C. and a relative humidity of 62±5%. The light-dark cycle was adjusted to 12 hours of light and 12 hours of darkness. The temperature and humidity were monitored and recorded by a breeder every day. Feeds and sterile reverse osmosis water were provided ad libitum. After one week of acclimation, the experiment was started.

2. Experimental Design

The shaved back skin of the mice was disinfected with povidone iodine solution. A splint was fixed on both sides of the mice with silicone, and then a wound with a skin removal area of 1 cm*1 cm and a depth of about 4-5 mm was made by surgical trauma. After 1 hour of trauma, the total 12 mice were divided into groups: a control group treated with saline (n=6) and a GKM3 group treated with GKM3 fermentation filtrate (n=6). The dressing was continuously given. The wound healing level in the animals was observed on days 0, 2, 4, 6, 8 and 10 after wound formation respectively, and the wound healing area was calculated and converted. The security index was used to determine that there was no health damage to the experimental animals. After the test substance was administered, in this experiment, analgesics were given by intramuscular injection every day within three days after the operation at a dose of 1 mg/kg. The dressing was changed every two days, and wound healing was photographed and the area was calculated. The results were shown in FIG. 1 and FIG. 2.

3. Experimental Results

In this experiment, wounds of the same range and the same degree were made on the skin of the mice, and treated with saline (control group) and a concentrated filtrate of probiotic GKM3 fermentation (GKM3 group), respectively, and the wound healing of the mice was observed for 10 days. Here, the concentrated filtrate of probiotic GKM3 fermentation was a supernatant obtained from 16 h fermentation of MRS culture by GKM3 and centrifugation to remove the bacteria, which was concentrated by 10 times by means of concentration under reduced pressure, equivalent to 10% of an initial volume of the fermentation substrate.

Referred to FIG. 1, which showed the appearance changes of the mouse skin wounds administered with the concentrated filtrate from probiotic GKM3 fermentation (GKM3 group) or saline (control group) at different time points according to one embodiment of the present disclosure. The appearance results in FIG. 1 showed that the skin wounds of mice in the GKM3 group had faster healing speed, and suppuration was hardly found in the wounds, and the degree of healing is higher. As observation days increased, the wounds of mice in the GKM3 group had faster healing speed and their healing degree was higher.

Figure 2:
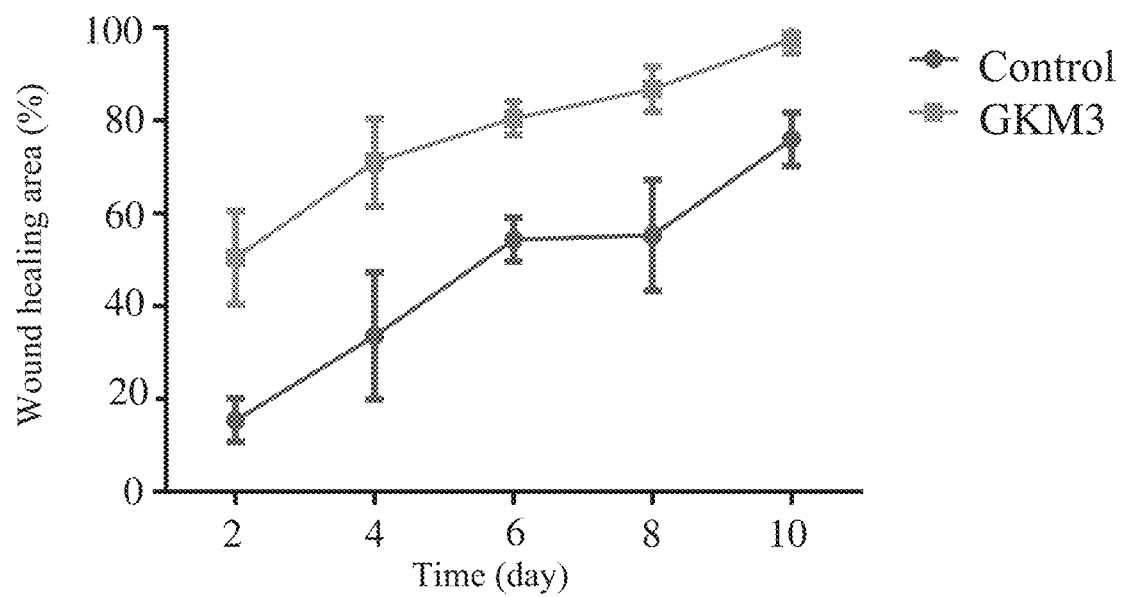
FIG. 2 shows the wound healing graphs of mouse skin wounds administered with a concentrated filtrate from probiotic GKM3 fermentation (GKM3 group) or saline (control group) at different time points according to one embodiment of the present disclosure.

Referred to FIG. 2, which showed the wound healing graphs of the mouse skin wounds administered with the concentrated filtrate from probiotic GKM3 fermentation (GKM3 group) or saline (control group) at different time points according to one embodiment of the present disclosure. The wound healing percentage results in FIG. 2 showed that the skin wounds of mice in the GKM3 group had greater wound healing area %, indicating that the degree of wound healing was better. On day 2 of the experiment, the wound healing rate of the GKM3 group reached 50%, while the wound healing rate of the control group was only about 15%. Till day 6 of the experiment, the wound healing rate of the GKM3 group reached about 80%, while the wound healing rate of the control group was only 54%. Till day 10 of the experiment, the wound healing rate of the GKM3 group reached 97%, while the wound healing rate of the control group was about 79%.

Moreover, in the mouse group given with the filtrate from probiotic GKM3 fermentation, suppuration was hardly found in the wounds and the wounds had faster healing speed. According to the experimental results, when the filtrate from *Lactobacillus plantarum* GKM3 fermentation was applied as a dressing of mouse skin wounds, the dressing of such a composition had the ability to improve wound suppuration and could promote skin wound healing.

In summary, it is demonstrated by the above several embodiments that the *Lactobacillus* fermentation product of the present disclosure using a bacteria-free concentrated filtrate from fermentation by a certain strain of *L. plantarum* can serve as an effective component, and indeed has the effects of inhibiting skin wound inflammation and promoting wound healing after administered to skin wounds.

It should be noted that although the present disclosure takes a specific manufacturing process, a specific absorptive carrier or carrying agent, or a specific analysis method as examples to illustrate the external composition for wound healing containing a *Lactobacillus* fermentation product of the present disclosure, anyone of ordinary skill in the art of the present disclosure can understand that the present disclosure is not limited thereto, and the external composition for wound healing containing a *Lactobacillus* fermentation product of the present disclosure can also be made using other manufacturing processes, other absorbent carriers or carrying agents or other analysis methods, without departing from the spirit and scope of the present disclosure.

It can be seen from the above examples that the external composition for wound healing containing a *Lactobacillus* fermentation product of the present disclosure is advantageous in that a bacteria-free concentrated filtrate from fermentation by a certain strain of *L. plantarum* is used as an effective component and the effective component is loaded on a pharmaceutically acceptable absorptive carrier or carrying agent, so that the resulting external composition for wound healing has the effects of inhibiting skin wound inflammation and promoting wound healing after administered to skin wounds.

Although the present disclosure has been disclosed with several examples as above, these examples are not intended to limit the present disclosure. Anyone of ordinary skill in the art of the present disclosure can make various changes and modifications without departing from the spirit and scope of the present disclosure. Therefore, the scope of the present disclosure shall be subject to those defined by the attached claims.

What is claimed is:

1. A method for promoting wound healing using an external composition, comprising:
    administering a composition comprising a *Lactobacillus* fermentation product as an effective component onto a skin of a subject in need thereof, wherein the *Lactobacillus* fermentation product is a bacteria-free concentrated filtrate from a fermentation step, a solid-liquid separation step and a concentration step of a fermentation substrate by *Lactobacillus*, the concentrated filtrate is concentrated to 5% to 20% of an initial volume of the fermentation substrate, the *Lactobacillus* is *Lactobacillus plantarum* GKM3 (deposited in China General Microbiological Culture Collection Center (CGMCC) with a deposition number of CGMCC 14565 on Aug. 25, 2017, and in Bioresource Collection and Research Center (BCRC) of Food Industry Research and Development Institute of the Republic of China, No. 331 Food Road, Hsinchu, Taiwan with deposit date of Jul. 14, 2017 and deposit number of BCRC 910787), and the fermentation substrate is selected from a group consisting of MRS agar, PCA agar, M17 agar, Rogosa agar, TOS-MUP agar, and any combination thereof; and
    a pharmaceutically acceptable absorbent carrier or carrying agent for loading the effective component.

2. The method for promoting wound healing using an external composition according to claim 1, wherein the *Lactobacillus* fermentation product has anti-inflammatory and healing promoting effects on a skin wound.

3. The method for promoting wound healing using an external composition according to claim 1, wherein the absorbent carrier is selected from a group consisting of a fiber carrier, a breathable film carrier, a hydrogel carrier, a gel carrier, a foam carrier, an algin carrier, a protein carrier, and any combination thereof.

4. The method for promoting wound healing using an external composition according to claim 1, wherein the carrying agent comprises an atomizing agent, and the external composition for wound healing is an aerosol.

5. The method for promoting wound healing using an external composition according to claim 1, wherein the effective component further comprises a medicinal component.

* * * * *